United States Patent
Hyun

(10) Patent No.: US 8,296,951 B2
(45) Date of Patent: Oct. 30, 2012

(54) METHOD OF MANUFACTURING A FIXTURE OF A DENTAL IMPLANT

(76) Inventor: Young Keun Hyun, Seoul (KR)

(*) Notice: Subject to any disclaimer, the term of this patent is extended or adjusted under 35 U.S.C. 154(b) by 0 days.

(21) Appl. No.: 12/821,280

(22) Filed: Jun. 23, 2010

(65) Prior Publication Data

US 2010/0330534 A1    Dec. 30, 2010

(30) Foreign Application Priority Data

Jun. 25, 2009  (KR) ................. 10-2009-0057048
Jun. 29, 2009  (KR) ................. 20-2009-0008318 U

(51) Int. Cl.
*A61C 5/09*    (2006.01)
*A61C 8/00*    (2006.01)

(52) U.S. Cl. ................. 29/896.1; 433/174

(58) Field of Classification Search ........... 29/896.1; 433/174, 173, 192, 201.1, 207, 219–221, 433/223

See application file for complete search history.

(56) References Cited

U.S. PATENT DOCUMENTS

| | | | |
|---|---|---|---|
| 5,078,607 A | 1/1992 | Niznick | |
| 5,316,476 A | 5/1994 | Krauser | |
| 5,324,199 A | 6/1994 | Branemark | |
| 5,601,553 A * | 2/1997 | Trebing et al. | 606/86 B |
| 5,620,323 A * | 4/1997 | Bressman et al. | 433/174 |
| 5,947,735 A * | 9/1999 | Day | 433/173 |
| 6,220,861 B1 | 4/2001 | Kwon et al. | |
| 6,981,873 B2 * | 1/2006 | Choi et al. | 433/173 |
| 2004/0006346 A1 * | 1/2004 | Holmen et al. | 606/73 |
| 2007/0172796 A1 | 7/2007 | Hyun et al. | |

* cited by examiner

*Primary Examiner* — Sarang Afzali
(74) *Attorney, Agent, or Firm* — Ladas & Parry LLP

(57) ABSTRACT

Provided are a method of manufacturing a fixture of a dental implant with an improved structure in which the performance of osseointegration is excellent, spread of inflammation is reduced and a combination force between the fixture and an alveolar bone is remarkably increased, and a fixture of a dental implant manufactured by the method. The performance of osseointegration is excellent, and spread of inflammation can be reduced, and a combination between the fixture and an alveolar bone can be remarkably improved. Furthermore, the fixture of the dental implant having the above structure can be easily manufactured.

10 Claims, 10 Drawing Sheets

ND OF A DENTAL IMPLANT

METHOD OF MANUFACTURING A FIXTURE OF A DENTAL IMPLANT

CROSS-REFERENCE TO RELATED PATENT APPLICATION

This application claims the benefit of Korean Patent Application No. 10-2009-0057048, filed on Jun. 25, 2009 and Korean Utility Model Application No. 20-2009-0008318 filed on Jun. 29, 2009, in the Korean Intellectual Property Office, the disclosure of which is incorporated herein in its entirety by reference.

BACKGROUND OF THE INVENTION

1. Field of the Invention

The present invention relates to a fixture of a dental implant and a method of manufacturing the same, and more particularly, to a fixture of a dental implant that allows fast bone formation at an early stage and prevents infection and inflammation, and a method of easily manufacturing the fixture.

2. Description of the Related Art

Generally, dental implants include a fixture, an abutment, and a crown.

A male screw portion is formed in the fixture, is inserted in an alveolar bone of a human body and supports and fixes a dental implant.

The abutment is combined with an upper portion of the fixture and is exposed to an upper portion of gingiva.

The crown is one kind of prosthesis that replaces natural tooth, is engaged with the abutment and is adhered and fixed to the abutment.

In order to achieve the success of implants, osseointegration between the fixture and the alveolar bone has to be successfully performed. When osseointegration is not successfully done, bone resorption or progressive bone loss occurs.

It is widely known that a surface roughness of the fixture affects the success of osseointegration. When the surface of the fixture becomes rough by increasing the surface roughness of the fixture, a contact surface between the implant and a surrounding bone is increased, and cell adsorption is improved, so that positive effects can be obtained.

However, the rough surface of the fixture promotes progress of infection when inflammation occurs around the implant. In other words, it is reported that, when the surface of the fixture is more rough than a polished surface, infection progresses more quickly along the surface of the fixture.

In order to solve the problem, as illustrated in FIG. 1, U.S. patent application Ser. No. 11/625,701 discloses an 'osseointegrated dental implant' in which the surface of a fixture 1 is overall rough and a polished band 3 having a low surface roughness is formed in a waist portion of a screw portion 2 of the fixture 1 so as to improve the performance of osseointegration and prevent progress of inflammation around a dental implant due to the polished band 3.

A method of manufacturing a fixture of a dental implant with an improved structure in which advantages of the implant having the above structure are maintained and simultaneously, a combination force between the fixture and the alveolar bone is further increased, is necessary.

SUMMARY OF THE INVENTION

The present invention provides a method of manufacturing a fixture of a dental implant with an improved structure in which the performance of osseointegration is excellent, spread of inflammation is reduced and a combination force between the fixture and an alveolar bone is remarkably increased, and a fixture of a dental implant manufactured by the method.

According to an aspect of the present invention, there is provided a method of manufacturing a fixture of a dental implant, the method including: cutting including forming a male screw portion of the fixture; fixing a ring-shaped protection jig by inserting the protection jig in the male screw portion of the fixture to surround portions of the male screw portion in a circumferential direction; performing surface processing on the male screw portion of the fixture to improve a surface roughness of the male screw portion; and removing the protection jig fixed on the male screw portion from the male screw portion of the fixture.

According to another aspect of the present invention, there is provided a fixture of a dental implant fixed on an alveolar bone, the fixture including: an upper screw portion formed as a screw having two threads; and a lower screw portion formed as a screw having one thread at a lower side of the upper screw portion, wherein portions of the upper screw portion are formed as a polished portion formed as a machined surface, and the remaining portions of the upper screw portion excluding the polished portion and the lower screw portion are formed as unpolished portions having higher surface roughnesses than a surface roughness of the polished portion, and a pitch of the upper screw portion is twice of a pitch of the lower screw portion.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The present invention will now be described more fully with reference to the accompanying drawings, in which exemplary embodiments of the invention are shown.

FIGS. 2 through 5 illustrate a method of manufacturing a fixture 100 of a dental implant, according to an embodiment of the present invention.

Figure 1:
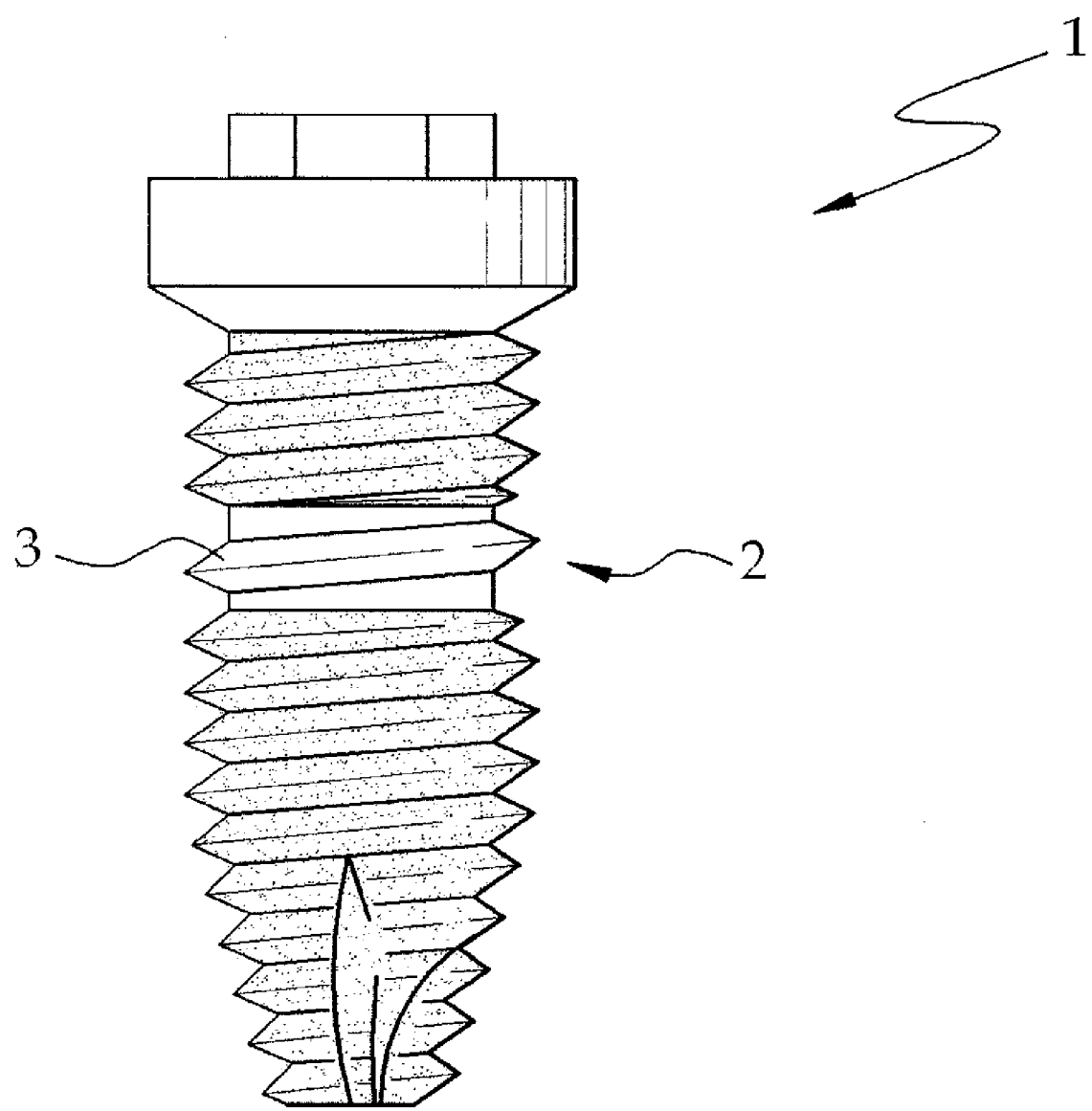
FIG. 1 is a front view of a structure of a conventional fixture of a dental implant.
Figure 2:
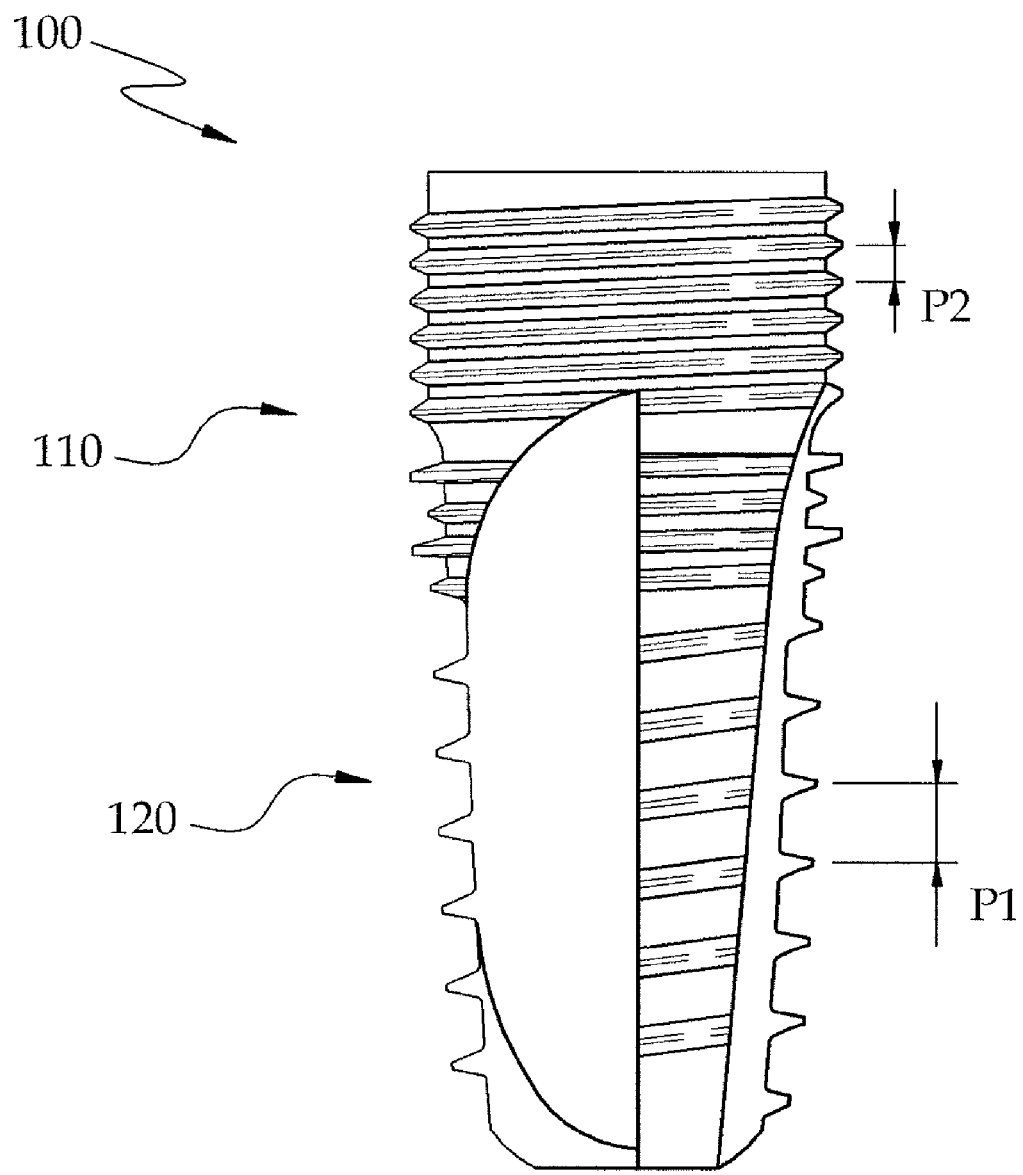
FIGS. 2 through 5 illustrate a method of manufacturing a fixture of a dental implant, according to an embodiment of the present invention, and a fixture of a dental implant manufactured by the method.

Referring to FIG. 2, the method of manufacturing the fixture 100 of the dental implant according to the current embodiment of the present invention includes cutting a screw portion including forming a lower screw portion 120 and an upper screw portion 110 by cutting the fixture 100 of the dental implant. Cutting of the screw portion is performed by two operations, i.e., forming of the lower screw portion 120 and forming of the upper screw portion 110. In the forming of the lower screw portion 120, the lower screw portion 120 is formed by cutting a screw having one thread at a lower side of the fixture 100. In the forming of the upper screw portion 110, the upper screw portion 110 is formed by cutting a screw having two threads at an upper side of the fixture 100. The order of forming of the lower screw portion 120 and forming of the upper screw portion 110 may be changed. In this regard, the cutting of the screw portion is performed so that a pitch P2 of the upper screw portion 110 may be twice of a pitch P1 of the lower screw portion 120. In this way, the pitch P2 of the upper screw portion 110 is twice of the pitch P1 of the lower screw portion 120 so that a lead of the lower screw portion 120 and a lead of the upper screw portion 110 may be synchronized with each other according to a rotation angle of the fixture 100.

A polished surface having a low surface roughness to a level of a machined surface is formed by a cutting tool of machine tools at the upper screw portion 110 and the lower screw portion 120. In this regard, the upper screw portion 110 and the lower screw portion 120 have an overall surface roughness in the rage of 0.2 to 0.7 μm.

Next, the method further includes performing surface processing on unpolished portions 112 and 121 that are the remaining portions of the fixture 100 excluding a polished portion 111 of a waist portion of the fixture 100 on which the cutting of the screw portion is completed, to improve surface roughnesses of the unpolished portions 112 and 121.

Surface processing is performed in the order of jig fixing, surface roughness improvement, and jig removal.

Figure 3:
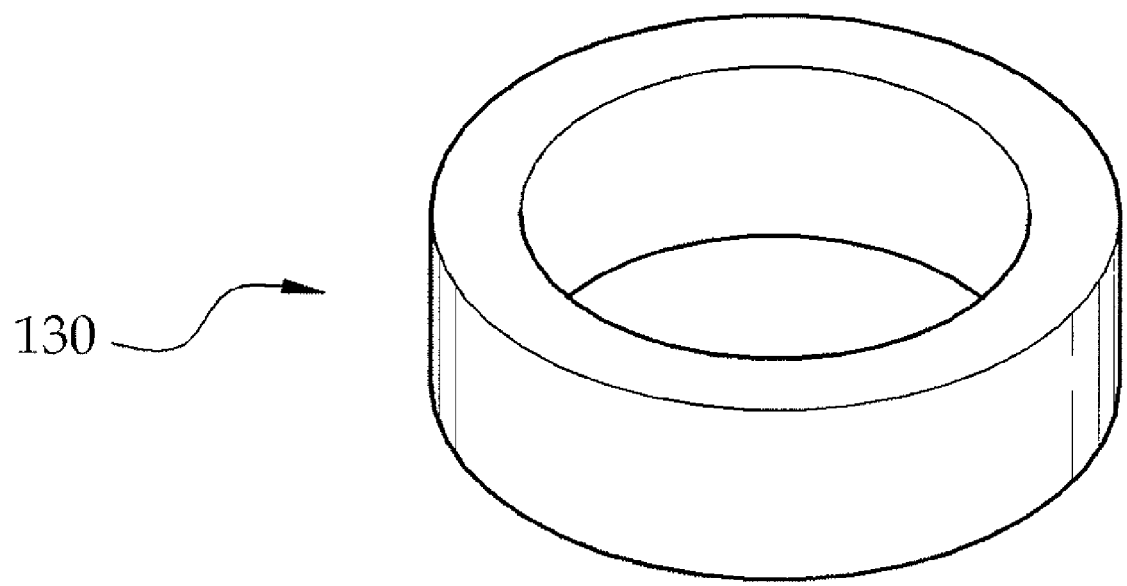

Surface processing is performed using a protection jig 130 illustrated in FIG. 3.

The protection jig 130 is ring-shaped and may be formed of synthetic resin having elasticity.

Figure 4:
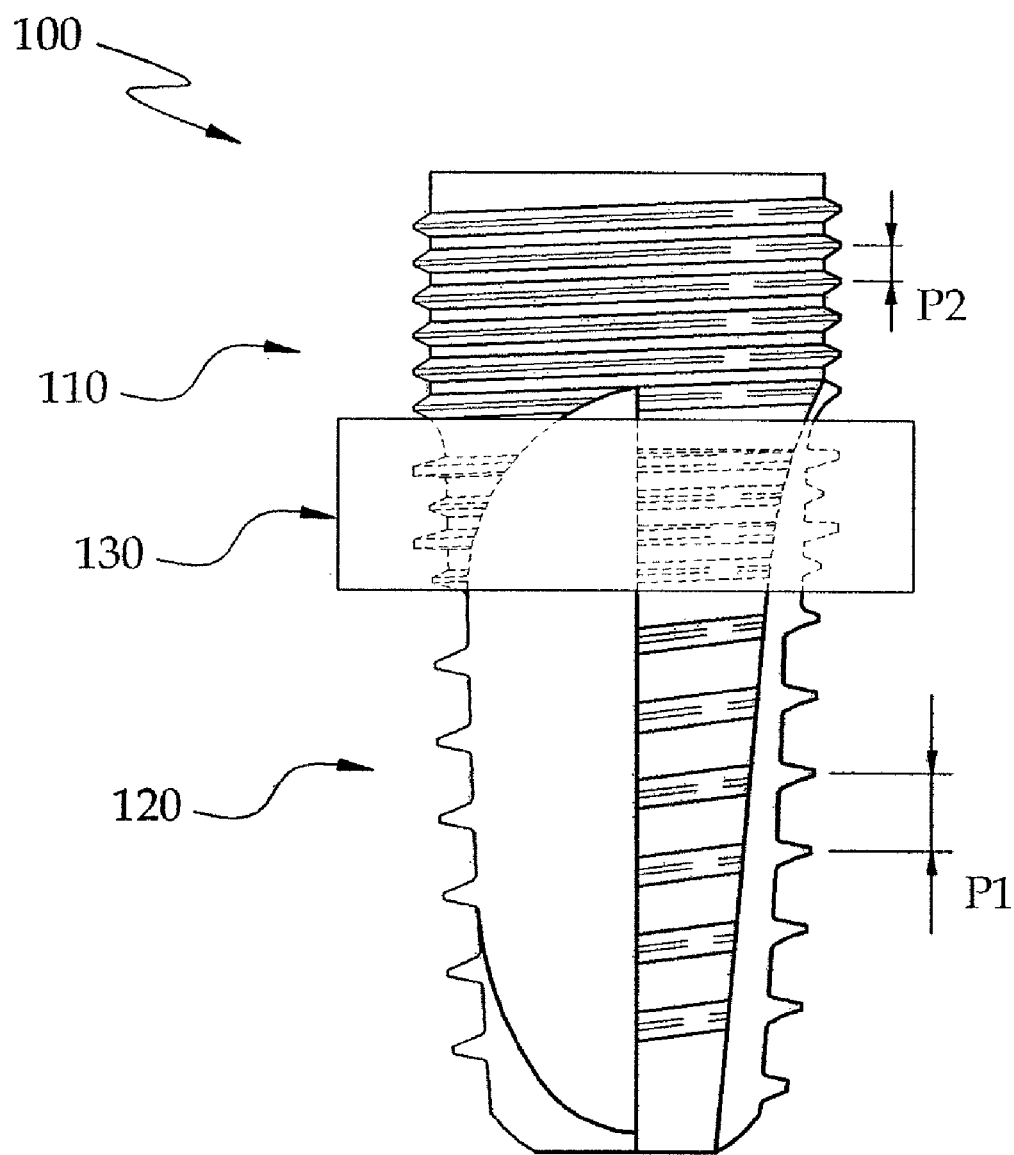

Jig fixing is performed in such a way that the protection jig 130 is inserted in the fixture 100 to surround portions of the upper screw portion 110 of the fixture 100 in a circumferential direction, as illustrated in FIG. 4.

When the protection jig 130 is pushed into the upper screw portion 110 of the fixture 100, the protection jig 130 is elastically deformed to securely surround an outer diameter of the upper screw portion 110 of the fixture 100. In the present embodiment, protection jig fixing is performed in such a way that the protection jig 130 is located at a lower side of the upper screw portion 110 that is adjacent to the lower screw portion 120. As occasions demand, a female screw portion is formed at an inner diameter of the protection jig 130 to be engaged with the upper screw portion 110 so that the female screw portion may be combined with the upper screw portion 110 of the fixture 100.

In this state, surface roughness improvement is performed by performing surface processing on the upper screw portion 110 and the lower screw portion 120 of the fixture 100. In other words, surfaces of the remaining portions (unpolished portions 112 and 121) of the fixture 100 excluding portions surrounded by the protection jig 130, of the upper screw portion 110 and the lower screw portion 120 of the fixture 100 are made rough. Surface roughness improvement may be performed by a method, such as sandblasting, anodization, etching, or the like. Such surface processing is performed so that the surface roughnesses of the unpolished portions 112 and 121 are between 1.2 and 2.0 μm.

In this state, jig removal is performed in such a way that the protection jig 130 fixed on the upper screw portion 110 is removed from the upper screw portion 110 of the fixture 100.

Figure 5:
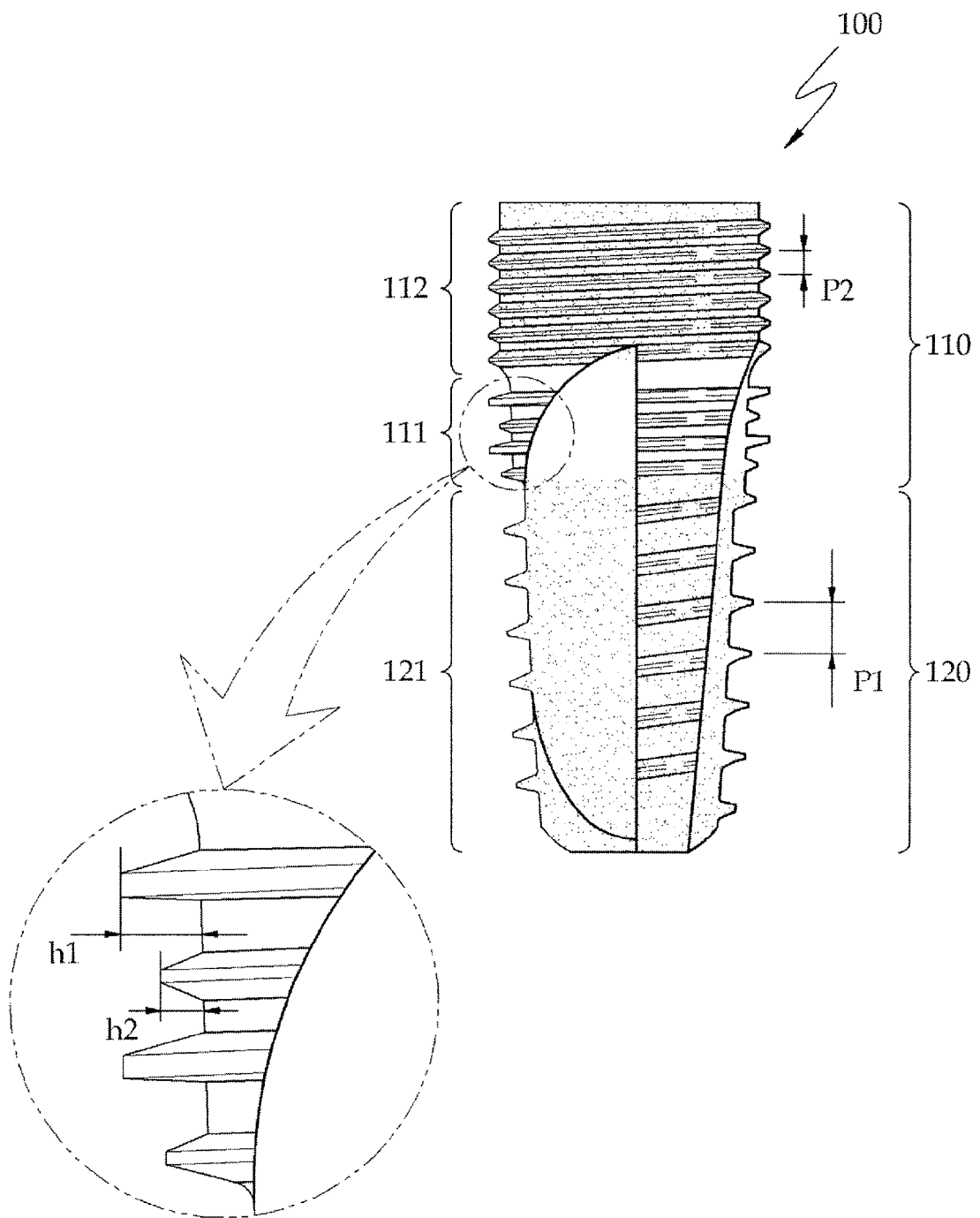

Referring to FIG. 5, portions of the upper screw portion 110 in which the protection jig 130 is inserted, are not surface-processed but are maintained in the state of a low surface roughness and become the polished portion 111. Since protection jig fixing is performed in such a way that the protection jig 130 is located at the upper screw portion 110 that is adjacent to the lower screw portion 120, as described above, the polished portion 111 is formed at a lower side of the upper screw portion 110 that is adjacent to the lower screw portion 120. The remaining portions of the upper screw portion 110 and the lower screw portion 120 excluding the polished portion 111 are surface-processed and become the unpolished portions 112 and 121 having surfaces that are more rough than the surface of the polished portion 111.

In the fixture 100 of the dental implant manufactured by the method, a degree of osseointegration is improved due to the unpolished portions 112 and 121 having high surface roughnesses, and inflammation may be prevented from being spread due to the polished portion 111 having a low surface roughness. Also, in the method of manufacturing the fixture 100 of the dental implant described above, the polished portion 111 may be easily formed at the fixture 100 of the dental implant having the above effects so that productivity of the fixture 100 may be improved.

Also, since the lower screw portion 120 of the fixture 100 is formed as a screw having one thread and the upper screw portion 110 thereof is formed as a screw having two threads, when a surgical procedure of the fixture 100 is performed, the lower screw portion 120 is inserted in an alveolar bone in a state where the position and angle of the lower screw portion 120 are easily fixed. After insertion of the lower screw portion 120 is completed to some extent, a combination force between the fixture 100 and the alveolar bone is improved while the upper screw portion 110 formed as a screw having two threads is inserted in the alveolar bone. Also, due to the upper screw portion 110, after the surgical procedure of the fixture 100 is completed, as time elapses, an area in which the tissues of the human body contact surroundings of the fixture 100 is increased. Thus, it can be expected that the combination force between the fixture 100 and the alveolar bone may be further improved as time elapses.

Meanwhile, in the above-described forming of the upper screw portion 110, portions to correspond to the polished portion 111 of the upper screw portion 110 may be processed as follows. In detail, when one of two threads of the screw having two threads of the polished portion 111 is referred to as a first thread and the other one thereof is referred to as a second thread, a height h2 of the first thread may be 30 to 80% of a height h1 of the second thread. When the height h2 of the first thread is less than 30% of the height h1 of the second thread, the combination force between the fixture 100 and the alveolar bone or a contact surface between the implant and a surrounding bone may be reduced. When the height h2 of the first thread is greater than 80% of the height h1 of the second thread, it may be difficult to fix the protection jig 130.

The fixture 100 of the dental implant manufactured by the method illustrated in FIGS. 2 through 5 described above includes the upper screw portion 110 and the lower screw portion 120. As described above, an upper portion of the fixture 100 of the dental implant is cut by the screw having two threads, and a lower portion thereof is cut by the screw having one thread.

As illustrated in FIG. 5, the portions of the upper screw portion 110 in which the protection jig 130 is inserted, are not surface-processed but are maintained in the state of a low surface roughness and become the polished portion 111. Also, the remaining portions of the upper screw portion 110 and the lower screw portion 120 excluding the polished portion 111 are surface-processed and become the unpolished portions 112 and 121 having surfaces that are more rough than the surface of the polished portion 111.

Also, the lower screw portion 120 of the fixture 100 is formed as the screw having one thread, and the upper screw portion 110 thereof is formed as the screw having two threads.

Also, the threads of the screw having two threads of the polished portion 111 may be trapezoidal.

Next, a method of manufacturing a fixture of a dental implant, according to another embodiment of the present invention will be described.

FIGS. 6 through 9 illustrate a method of manufacturing a fixture 200 of a dental implant, according to another embodiment of the present invention.

Figure 6:
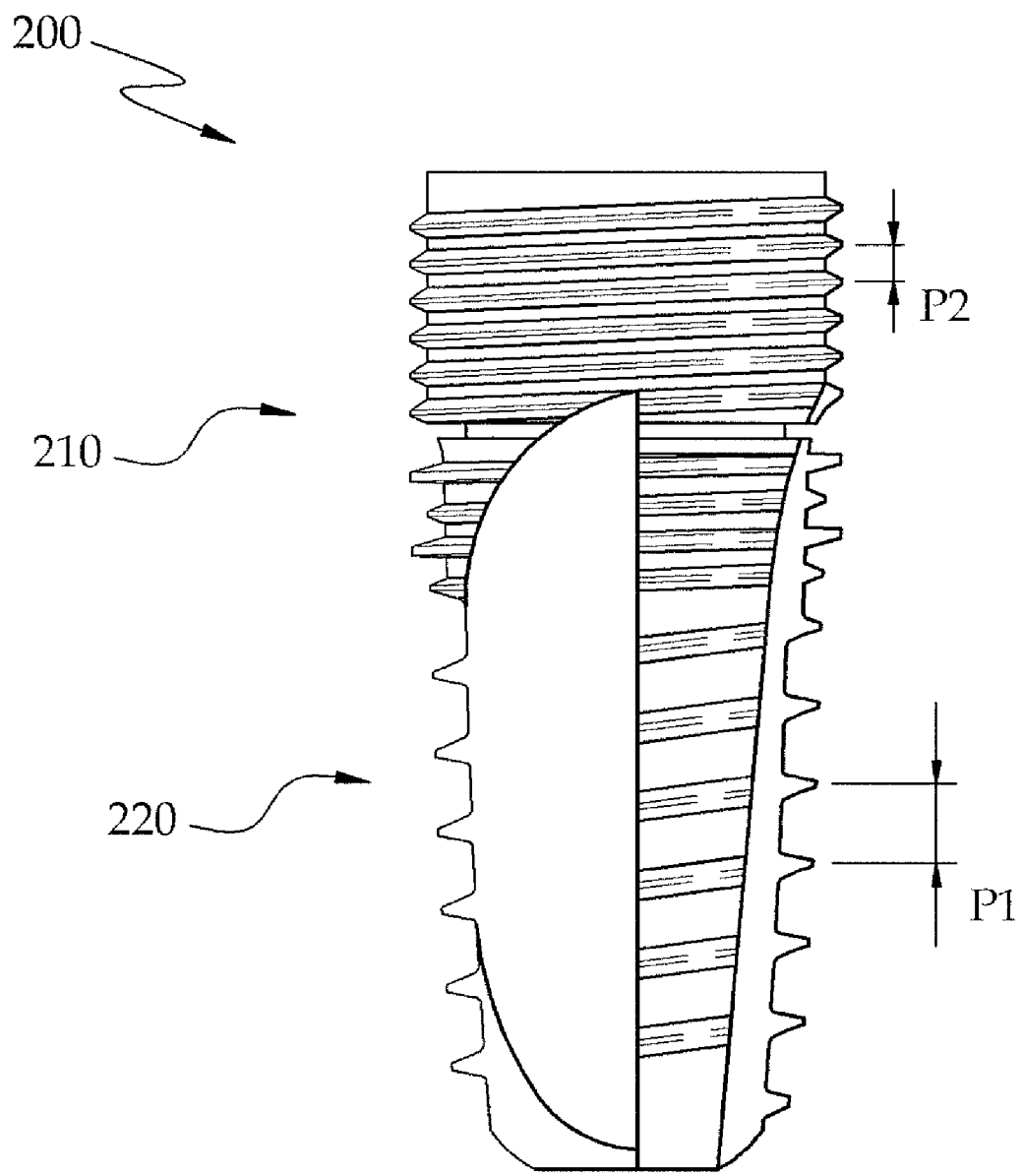
FIGS. 6 through 9 illustrate a method of manufacturing a fixture of a dental implant, according to another embodiment of the present invention, and a fixture of a dental implant manufactured by the method.

Referring to FIG. 6, the method of manufacturing the fixture 200 of the dental implant according to the current embodiment of the present invention includes cutting a screw portion by forming a lower screw portion 220 including a screw having one thread at a lower side of the fixture 200 of the dental implant and by forming an upper screw portion 210 including a screw having two threads at an upper side of the fixture 200.

Next, as illustrated in FIG. 6, forming of a fixed groove 213 is performed in such a way that the fixed groove 213 is formed in the upper screw portion 210 of the fixture 200 to surround portions of the upper screw portion 210 in a circumferential direction.

By performing the cutting of the screw portion and the fixing of the fixed groove 213, the upper screw portion 210 and the lower screw portion 220 have surface roughnesses in the range of 0.2 to 0.7 μm.

Figure 7:
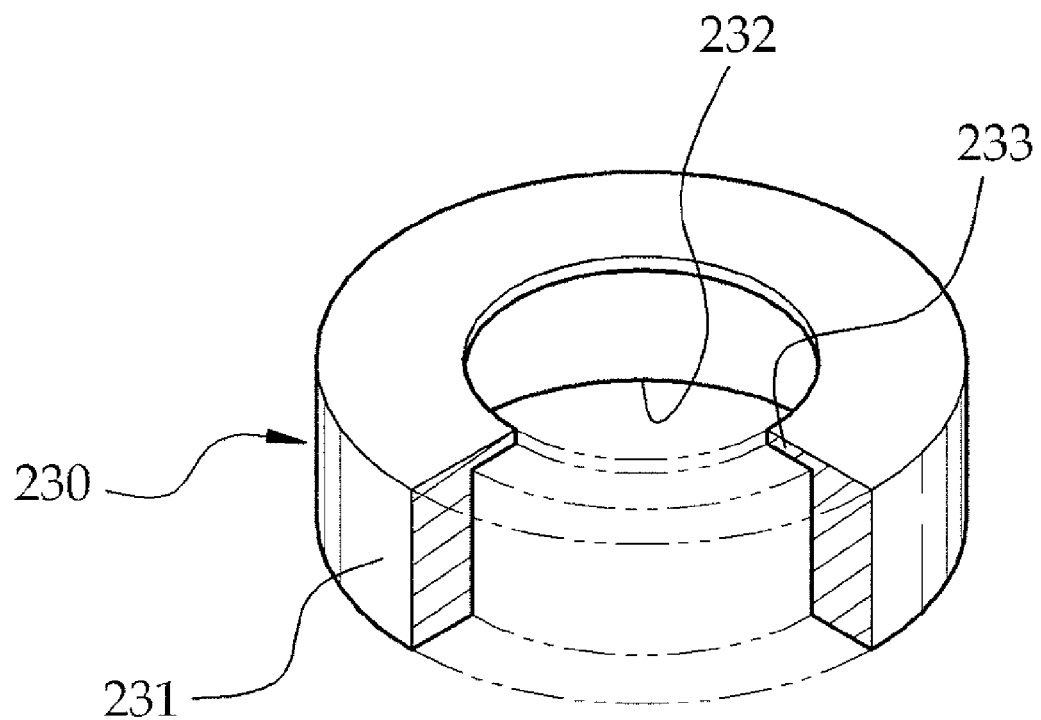

Meanwhile, a protection jig 230 is formed, as illustrated in FIG. 7. The protection jig 230 includes a body portion 231 and fixed protrusion 233. A combination hole 232 is formed in the body portion 231, and an inner diameter of the combination hole 232 is equal to or slightly smaller than an outer diameter of the upper screw portion 210. The fixed protrusion 233 is formed in the internal side of the combination hole 232 so as to be inserted in the fixed groove 213 of the fixture 200 and fixed therein. The fixed protrusion 233 is ring-shaped, and may be formed of synthetic resin having elasticity.

Now, surface processing for improving surface roughnesses of unpolished portions 212 and 221 by using the protection jig 230 is performed. Surface processing is performed in the order of jig fixing, surface roughness improvement, and jig removal.

Figure 8:
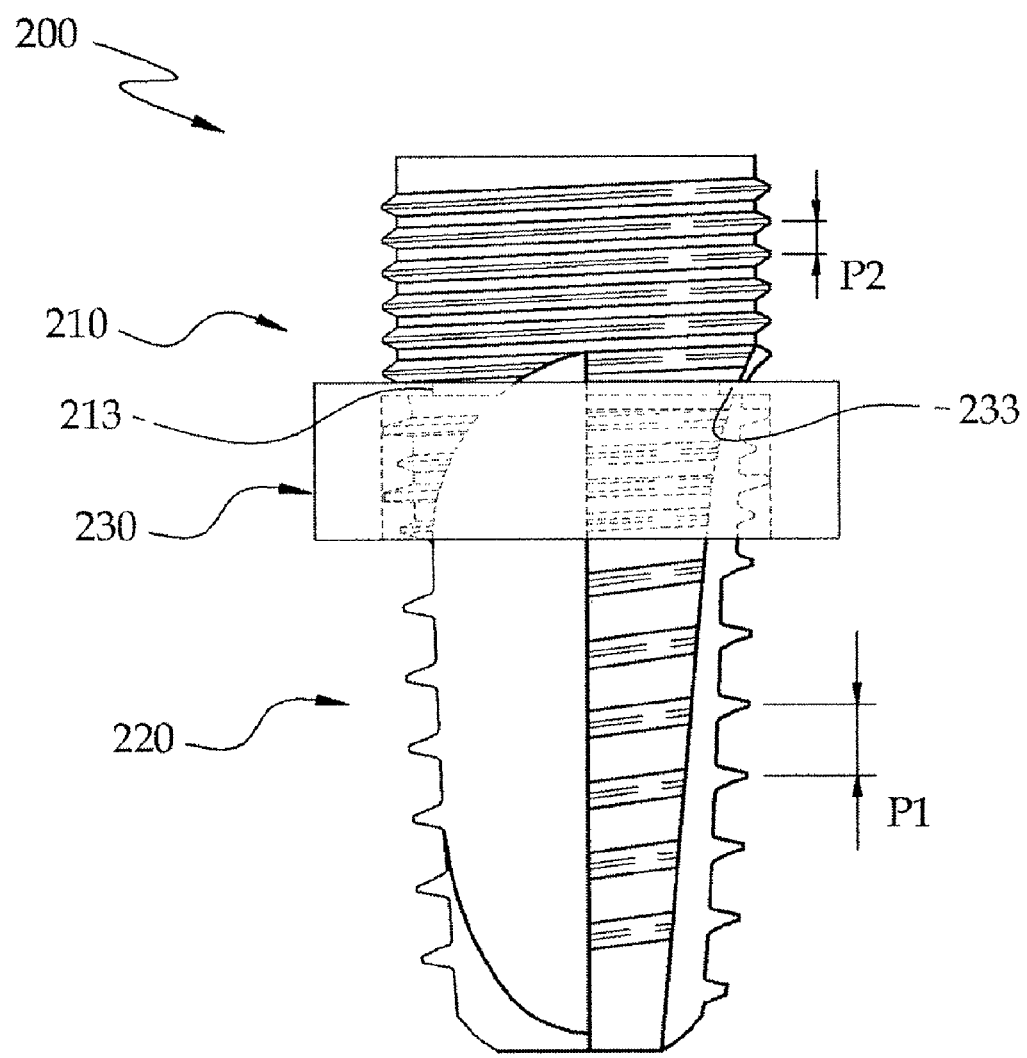

Jig fixing is performed in such a way that the protection jig 230 is inserted in the upper screw portion 210 of the fixture 200 to surround portions of the upper screw portion 210 in the circumferential direction, as illustrated in FIG. 8. In this regard, the fixed protrusion 233 of the protection jig 230 inserted in the fixed groove 213 of the fixture 200 so that the protection jig 230 may not be shaken with respect to the fixture 200 and may be securely fixed on the fixture 200.

In this state, surface roughness improvement by performing surface processing on the upper screw portion 210 of the fixture 200 is performed. In detail, surfaces of the remaining portions of the fixture 200 excluding a polished portion 211 are made rough. When performing surface roughness improvement, sandblasting, anodization, etching, or the like may be used.

When surface roughness improvement is performed using sandblasting, the surfaces of the remaining portions of the fixture 200 excluding the polished portion 211 are made rough by ejecting an abrasive into the upper screw portion 210 and the lower screw portion 220 at high speed. When the abrasive ejected into the upper screw portion 210 and the lower screw portion 220 at high speed collides with the protection jig 230, the protection jig 230 may be shaken with respect to the upper screw portion 210 and may be escaped therefrom during the procedure. Since a fixture of a dental implant that is recently used mostly has a tapered male screw portion and an outer diameter of the fixture is downwardly reduced, a possibility in which the protection jig 230 may be escaped from the upper screw portion 210 is increased.

However, as illustrated in FIG. 8, when the fixed protrusion 233 of the protection jig 230 and the fixed groove 213 of the fixture 200 are engaged with each other, the protection jig 230 is prevented from being escaped from the upper screw portion 210 so that a defect rate may be reduced, productivity may be improved and quality of the fixture 200 may be improved.

Next, jig removal is performed in such a way that the protection jig 230 fixed on the upper screw portion 210 is removed from the fixture 200.

Figure 9:
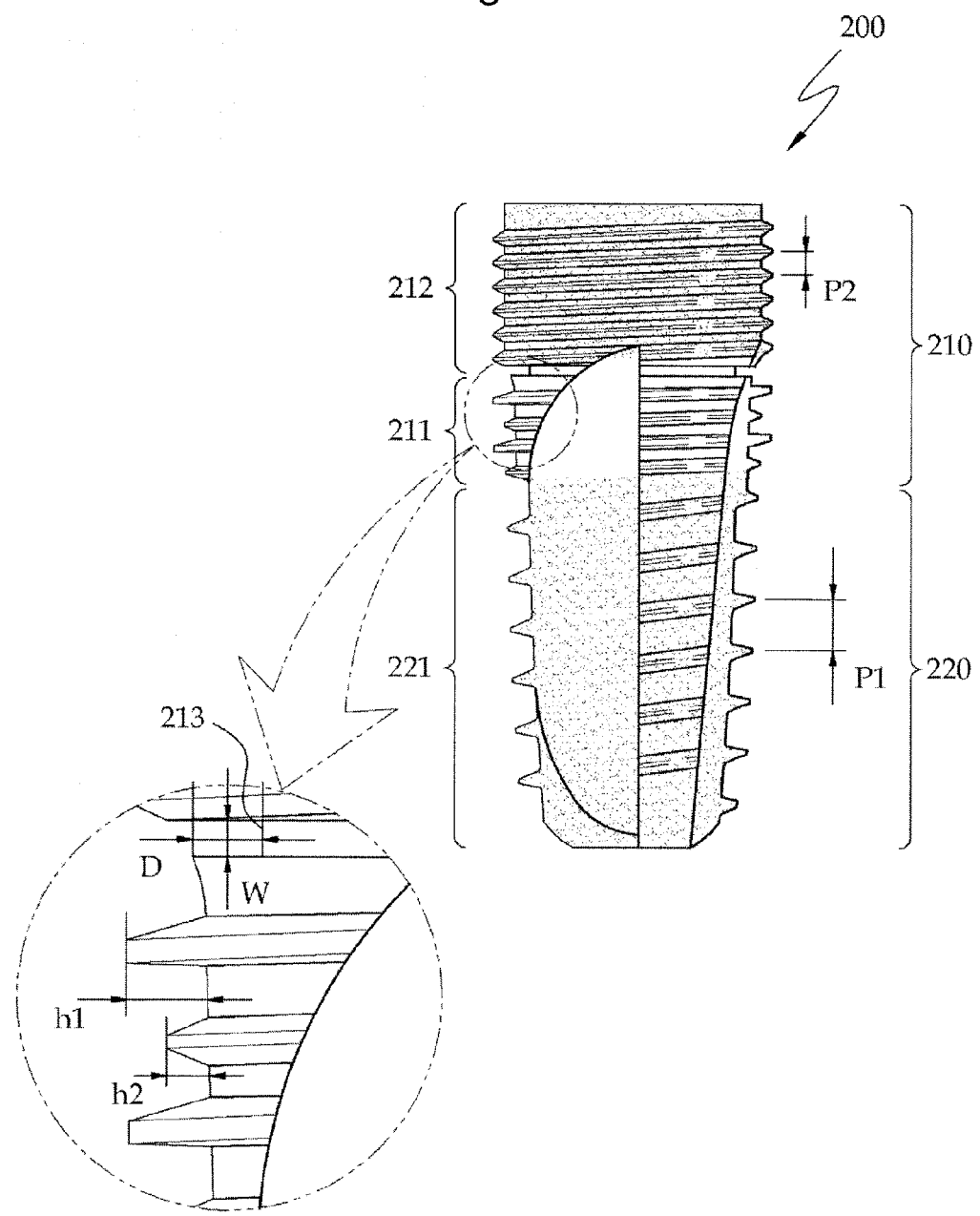

Referring to FIG. 9, portions of the upper screw portion 210 in which the protection jig 230 is inserted, are not surface-processed but are maintained in the state of a low surface roughness and become the polished portion 211, and the remaining portions of the upper screw portion 210 excluding the polished portion 211 and the lower screw portion 220 become unpolished portions 212 and 221 having rough surfaces. The surface roughnesses of the unpolished portions 212 and 221 may be between 1.2 to 2.0 μm.

Referring to FIG. 6, a width W of the fixed groove 213 may be between 0.1 to 0.5 mm. When the width W of the fixed groove 213 is less than 0.1 mm, the fixed protrusion 233 of the protection jig 230 may not be well inserted in the fixed groove 213, and when the width W of the fixed groove 213 is greater than 0.5 mm, portions of the upper screw portion 210 and the lower screw portion 220 in which no threads are formed, become so large and a combination force between the fixture 200 and the alveolar bone may be reduced.

Also, a depth D of the fixed groove 213 with respect to screw valleys of the upper screw portion 210 may be between 0.05 and 0.15 mm. When the depth D of the fixed groove 213 is less than 0.05 mm, the fixed protrusion 233 of the protection jig 230 may not be well inserted in the fixed grove 213, and when the depth D of the fixed groove 213 is greater than 0.15 mm, rigidity of the fixture 200 may be reduced.

Also, the polished portion 211 may be disposed in the range of 2 to 8 mm downwardly from an upper end of the upper screw portion 210. When the polished portion 211 is located in the range of 2 mm from the upper end of the upper screw portion 210, performance of preventing inflammation from being spread may be lowered, and when the polished portion 211 is located in the range of below 8 mm from the upper end of the upper screw portion 210, the combination force between the fixture 200 and the alveolar bone may be reduced.

The fixture 200 manufactured by the method illustrated in FIGS. 6 through 9 includes the lower screw portion 220 formed as a screw having one thread and the upper screw portion 210 formed as a screw having two threads, as illustrated in FIG. 6. The upper screw portion 210 of the fixture 200 includes the fixed groove 213 formed to surround portions of the upper screw portion 210 in the circumferential direction.

As illustrated in FIG. 9, portions of the upper screw portion 210 in which the protection jig 230 is inserted, are not surface-processed but are maintained in the state of a low surface roughness and become the polished portion 211, and the remaining portions of the upper screw portion 210 excluding the polished portion 211 become the unpolished portions 212 and 221 having rough surfaces.

In the fixture 200 of the dental implant according to the current embodiment, a degree of osseointegration is improved due to the unpolished portions 212 and 221 having high surface roughnesses, and inflammation is prevented from being spread due to the polished portion 211 having a low surface roughness. Also, in the fixture 200 of the dental implant having the above-described structure, the polished portion 211 may be easily formed in the fixture 200 of the dental implant having the above effects so that productivity of the fixture 200 may be improved.

Next, a method of manufacturing a fixture of a dental implant, according to another aspect of the present invention will be described.

Figure 10:
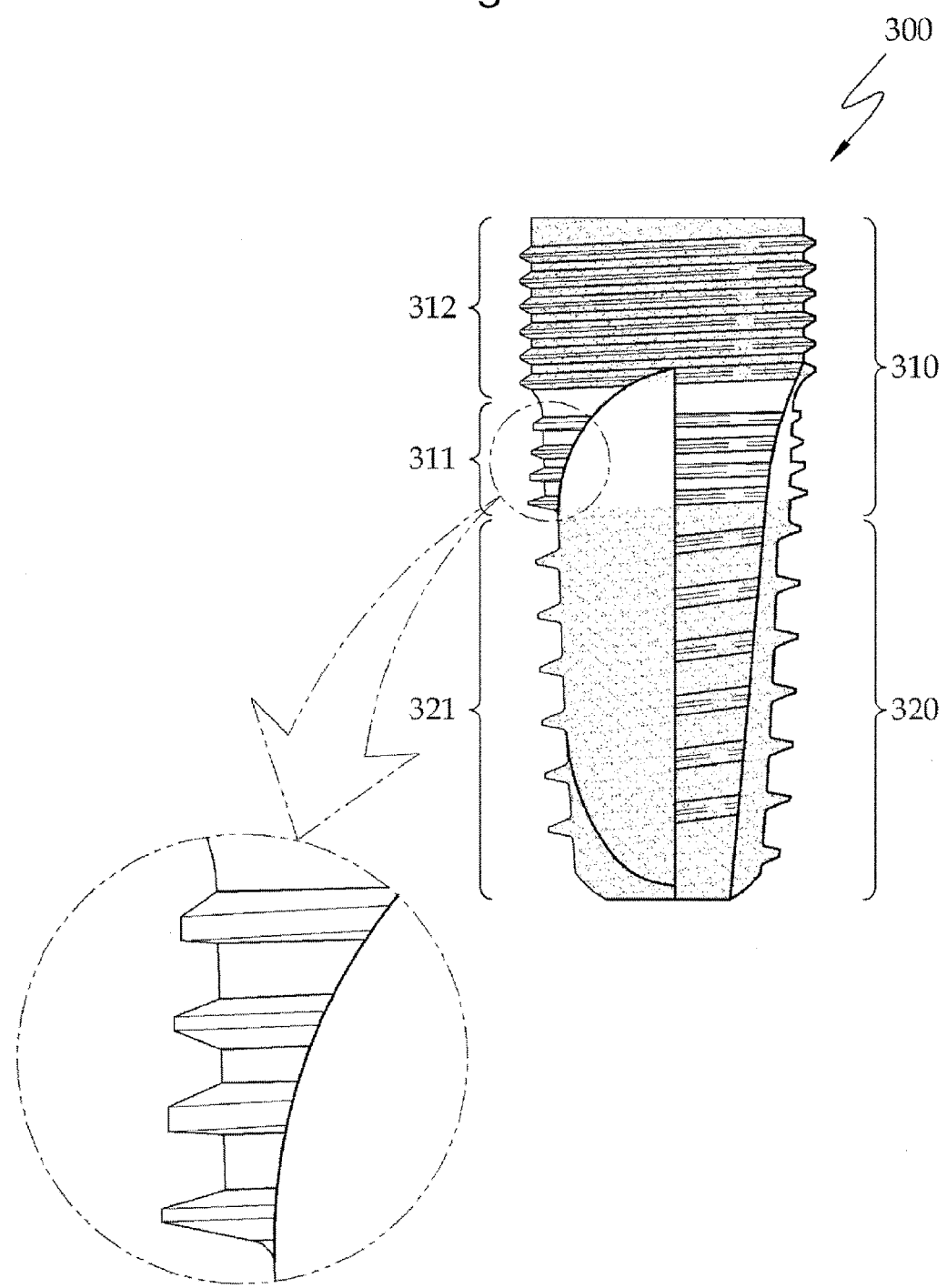
FIG. 10 illustrates a method of manufacturing a fixture of a dental implant, according to another embodiment of the present invention, and a fixture of a dental implant manufactured by the method.

FIG. 10 illustrates a method of manufacturing a fixture 300 of a dental implant, according to another embodiment of the present invention.

The method of manufacturing the fixture 300 of the dental implant according to the current embodiment of the present invention is very similar to the method illustrated in FIGS. 2 through 5. In detail, the method of FIG. 10 includes cutting a screw portion by forming a lower screw portion 320 at a lower side of the fixture 300 of the dental implant and by forming an upper screw portion 310 of the fixture 300. In this regard, as illustrated in FIG. 10, cutting of the screw portion is performed on portions that will correspond to a polished portion 311 so that the portions may have a higher thread as they are closer to a lower side thereof.

Next, surface processing for improving surface roughnesses of unpolished portions 312 and 321 is performed by forming the same protection jig 130 as illustrated in FIG. 3. Surface processing is performed in the order of jig fixing, surface roughness improvement, and jig removal. As illustrated in FIG. 10, since the thread of the polished portion 321 becomes higher as it is closer to its lower side, the protection jig 120 may not be shaken and may be securely fixed even when surface processing performed.

In the fixture 300 of the dental implant manufactured by the method of FIG. 10, the remaining portions of the fixture 300 excluding the polished portion 311 are the same as those of the fixture 100 of the dental implant manufactured by the method of FIGS. 2 through 5.

The lower screw portion 320 is formed as a screw having one thread, and the upper screw portion 310 is formed as a screw having two threads. The unpolished portions 312 and 321 have higher surface roughnesses than the surface roughness of the polished portion 321.

As described above, exemplary embodiments of the present invention have been described. However, aspects of the present invention are not limited thereto.

For example, the fixed protrusion 233 of the protection jig 230 of FIG. 7 are respectively located adjacent to an upper side of the body portion 231. However, as occasion demands, the fixed protrusion 233 may be located adjacent to a lower side of the body portion 231 or may be disposed at middle inner walls of the body portion 231.

As described above, in a fixture of a dental implant according to the present invention, the performance of osseointegration is excellent, and spread of inflammation can be reduced, and a combination between the fixture and an alveolar bone can be remarkably improved.

Furthermore, the fixture of the dental implant having the above structure can be easily manufactured.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of manufacturing a fixture of a dental implant, the method comprising:
   providing a polished surface of a screw portion by cutting the screw portion comprising forming a lower screw portion formed as a single-thread screw at a lower side of the fixture of the dental implant and forming an upper screw portion formed as a double-thread screw at an upper side of the fixture;
   forming a fixed groove in the upper screw portion of the fixture wherein the fixed groove surrounds the upper screw portion in a circumferential direction;
   inserting a ring-shaped protection jig in the fixed groove of the upper screw portion and fixing the protection jig to the fixed groove to surround a polished waist portion of the upper screw portion in a circumferential direction,
   wherein the protection jig is composed of a synthetic resin having elasticity, and
   wherein the protection jig comprises a body portion having a combination hole configured to be inserted and fixed in the upper screw portion of the fixture and a fixed protrusion is formed in an internal side of the combination hole which is configured to be engaged in the fixed groove of the upper screw portion and fixed therein;
   performing surface processing on the polished screw portion excluding the polished waist portion of the fixture which remains polished and surrounded by the protection jig, using sandblasting; and
   removing the protection jig fixed on the waist portion of the fixture thereby leaving exposed the polished waist portion.

2. The method of claim 1, wherein a pitch of the upper screw portion is twice of a pitch of the lower screw portion.

3. The method of claim 2, wherein the polished waist portion is disposed at a lower side of the upper screw portion that is adjacent to the lower screw portion.

4. The method of claim 3, wherein a height of a first thread of threads of the double-thread screw of the polished waist portion is 30 to 80% of a height of a second thread of the threads of the double-thread screw of the polished waist portion.

5. The method of claim 4, wherein threads of the double-thread screw of the polished portion are trapezoidal.

6. The method of claim 3, wherein the thread height from the surface of the screw portion of the polished waist portion becomes higher as the polished waist portion is closer to a lower side thereof.

7. The method of claim 1, wherein the fixed groove is formed to a depth between 0.05 and 0.15 mm with respect to screw valleys of the upper screw portion, and a width of the fixed groove is between 0.1 and 0.5 mm.

8. The method of claim 7, wherein the polished waist portion is disposed in a range of 2 to 8 mm downwardly from an upper end of the upper screw portion.

9. The method of claim 1, wherein a female screw portion is formed at an inner diameter of the protection jig to be engaged with the upper screw portion.

10. The method of claim 1, wherein a surface roughness of the polished waist portion is between 0.2 and 0.7 µm, and surface roughnesses of the surface processed portions are between 1.2 and 2.0 µm.

* * * * *